United States Patent [19]  
Kurabayashi et al.

[11] Patent Number: 4,564,675  
[45] Date of Patent: Jan. 14, 1986

[54] PROCESS FOR PRODUCING 4'-DEMETHYL-EPIPODOPHYLLOTOXIN-β-D-ETHYLIDENE-GLUCOSIDE AND ACYL-DERIVATIVE THEREOF

[75] Inventors: Katsuhiko Kurabayashi, Annaka; Hidefumi Kinoshita; Hitoshi Saito, both of Takasaki; Toshio Takahashi, Annaka, all of Japan

[73] Assignee: Nippon Kayaku Kabushiki Kaisha, Tokyo, Japan

[21] Appl. No.: 529,749

[22] Filed: Sep. 6, 1983

[30] Foreign Application Priority Data

Nov. 26, 1982 [JP] Japan .............................. 57-206188  
May 18, 1983 [JP] Japan .............................. 56-85868

[51] Int. Cl.$^4$ ........................................... C07H 15/24  
[52] U.S. Cl. .................................... 536/18.1; 536/4.1; 536/115  
[58] Field of Search ................... 536/18.1, 4.1, 115

[56] References Cited  
U.S. PATENT DOCUMENTS 3,524,844  8/1970  Keller-Juslen et al. ............ 536/18.1  
4,147,860  4/1979  Farnham et al. .................... 536/115

OTHER PUBLICATIONS

Migridichian *Organic Synthesis*, 1957, (p. 12).

Primary Examiner—Johnnie R. Brown  
Assistant Examiner—Elli Peselev  
Attorney, Agent, or Firm—Henry C. Nields

[57] ABSTRACT

Disclosed herein are a process for producing 4'-demethyl-epipodophyllotoxin-β-D-ethylidene-glucoside of the formula (II) comprising (A) reacting 4'-halogenoacetyl-4'-demethyl-epipodophyllotoxin-β-D-2,3-di-O-halogenoacetyl-4,6-O-ethylidene-glucoside of the formula (I) with an amine and/or ammonia, or (B) subjecting the acyl-derivative (I) to alcoholysis in the presence of a catalyst, thereby removing the halogenoacetyl groups of the acyl-derivative (I) to obtain the compound (II), the acyl-derivative (I), and the use of the acyl-derivative (I) for synthesizing the compound (II)

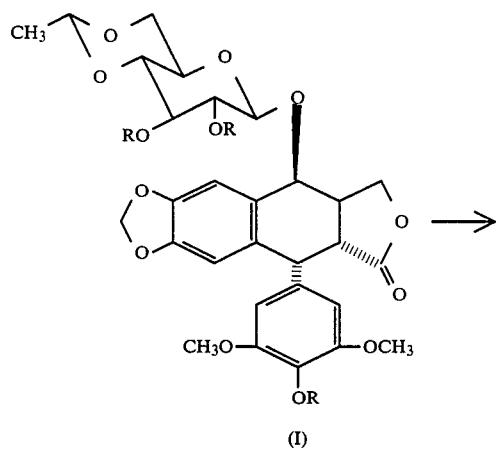

(I)

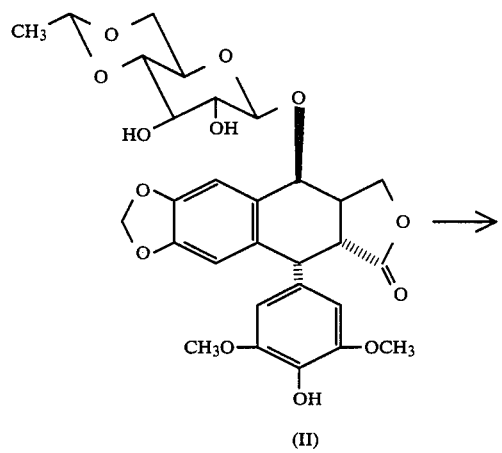

(II)

wherein R represents a halogenoacetyl group represented by the formula

—COCH$_2$X wherein X is a halogen atom.

9 Claims, No Drawings

PROCESS FOR PRODUCING 4'-DEMETHYL-EPIPODOPHYLLOTOXIN-β-D-ETHYLIDENE-GLUCOSIDE AND ACYL-DERIVATIVE THEREOF

DETAILED DESCRIPTION OF THE INVENTION

The present invention relates to a process for producing 4'-demethyl-epipodophyllotoxin-β-D-ethylidene-glucoside represented by the formula (II):

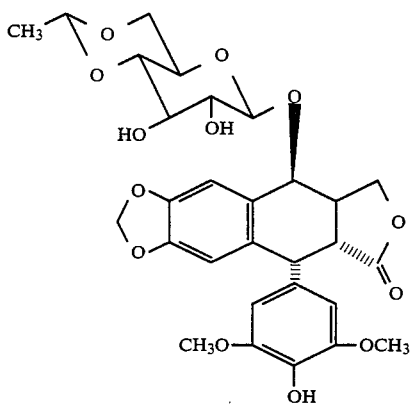

(II)

comprising (A) reacting 4'-halogenoacetyl-4'-demethyl-epipodophyllotoxin-β-D-2,3-di-O-halogenoacetyl-4,6-O-ethylidene-glucoside represented by the formula (I):

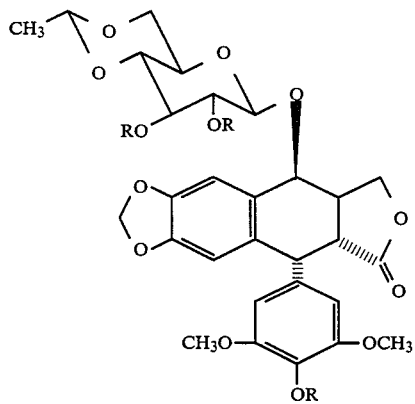

(I)

wherein R represents a halogenoacetyl group represented by the formula

—COCH₂X wherein X is a halogen atom, with an amine, or ammonia, or both; or (B) subjecting the acyl-derivative (I) to alcoholysis in the presence of a catalyst, thereby removing the halogenoacetyl groups to obtain the compound (II); the acyl-derivative (I); and the use of the acyl-derivative (I) for producing the compound (II).

In the following description by the term "an amine and/or ammonia" we mean an amine, or ammonia, or both.

The compound represented by the formula (II) is called as "ETOPOSIDE". The compound (II) shows an anti-tumour activity and is a useful substance as an anti-cancer medicine.

As a process for producing the compound (II), the processes disclosed in U.S. Pat. No. 3,524,844 and in Canadian Pat. No. 956,939 have been known. However, in these processes, the protecting group for the aglycone in the compound (I) and that for the sugar moiety therein differ to each other and accordingly, two steps are necessary to remove both the two kinds of protecting group. Namely, for the removal of a benzyloxycarbonyl group which is the protecting group for 4'-position of the aglycone, the starting compound is subjected to hydrogenolysis in the presence of palladium-carbon as a catalyst and further, for the removal of the acetyl group or the formyl group which is the protecting group for the sugar moiety, the de-benzyloxycarbonylated compound is subjected to alcoholysis by the use of zinc acetate. Particularly, the removal of the protecting groups for the sugar moiety necessitates a high temperature and a long time period of reaction, for instance, the reaction is not completed even by heating for 20 to 30 hours. Further, the amount of by-products increases with the lapse of the longer reaction time period and therefor, the yield of the product is reduced. Namely, the known processes are not favorable as industrial processes.

As a result of the present inventors' studies for overcoming the demerit of the known processes, it has been found by the present inventors that the halogenoacetyl groups (R) which are the protecting group for 4'-position of the aglycone and also the protecting groups for 2- and 3-positions of the sugar moiety in the compound (I) can be removed safely in one step in which the compound (I) is reacted with an amine and/or ammonia for a few hours at a temperature of 0° C. to room temperature, and the compound (II) of a high purity is obtained in a high yield.

Further, it has also been found by the present inventors that the halogenoacetyl groups (R) which protect 4'-position of aglycone and 2- and 3-positions of the sugar moiety can be removed from the compound (I) in one step by alcoholysis of the compound (I) within a very short period of 1 to 5 hours in the presence of a catalyst, preferably in the presence of one or more than one selected from the group consisting of zinc chloride, zinc acetate, zinc nitrate, zinc powder, lead acetate, lead powder, cadmium acetate, cobalt acetate, magnesium acetate, calcium acetate, strontium acetate, barium acetate and cerium acetate, and that the compound (II) of a high purity can be obtained in a high yield.

The halogenoacetyl groups (R) at 4'-position of the aglycone and 2- and 3-positions of the sugar moiety may be the same or different to each other. As an atom of halogen of X, chlorine and bromine are preferred.

The present invention will be explained in detail as follows:

(A) PROCESS FOR REMOVING THE HALOGENOACETYL GROUPS BY REACTING THE COMPOUND (I) WITH AN AMINE AND/OR AMMONIA

As the amine used in the present invention, an aliphatic primary amine such as methylamine, ethylamine, n-propylamine, n-butylamine and the like; an aliphatic secondary amine such as dimethylamine, diethylamine, di-n-propylamine, di-n-butylamine and the like; a cyclic amine such as pyrrolidine, piperidine, morpholine and the like; and an aliphatic diamine such as ethylenediamine and the like, may be mentioned. In the case where one of these amines and/or ammonia are (is) used, it is natural to add it (them) into the reaction system as it is and also, an acetate, a hydrochloride, etc. of the amine and/or ammonia may be added to the reaction system in the presence of a base such as pyridine, triethylamine and the like thereby producing the free amine and/or ammonia within the reaction system to use the thus liberated amine and/or ammonia. The amount of the amine and/or ammonia used in the reaction is suitably 3 to 10 times by mole of the amount of the compound (I).

The reaction temperature depends on the kinds of the amine. The reaction temperature is preferably −10° to 100° C. and particularly, 0° to 70° C. is preferable. The time for completing the reaction depends on the kinds of the amine and the reaction temperature, and usually it takes 0.5 to 5 hours.

As the solvent used in the present invention, there are no limitations unless the solvent exert a bad influence on the reaction and, for instance, chloroform, ethylene dichloride, methanol, ethanol and pyridine may be mentioned.

According to the process of the present invention, the removal of the halogenoacetyl groups (R) is easily effected in a short time period under mild reaction conditions to obtain the compound (II) in a high yield from the compound (I). Accordingly, the purification of the product after finishing the reaction is easily carried out. For instance, the purification is carried out only by washing the reaction mixture with water followed by simple recrystallization, thereby giving the pure compound (II). Consequently, the process mentioned above is an extremely profitable process as an industrial process.

Although the catalyst may be used in the state of a hydrate form, it is preferable to use the anhydride thereof. The amount of the catalyst used in the reaction is preferably 10 to 150% by weight of the compound (I).

As the alcohol for use in the reaction of the present process, methanol, ethanol, propanol and the like may be mentioned and particularly, it is industrially profitable to use methanol. Although the amount of the alcohol used therein is not particularly limited, it is preferable to use 20 to 200 times by weight of the compound (I).

The reaction is preferably carried out at a temperature of 40° to 100° C. and particularly, it is suitable to carry out the reaction at a reflux temperature of the alcohol for 1 to 5 hours.

According to the process of the present invention, since the removal of the halogenoacetyl groups is effected easily within a short time period, by-products are scarcely formed and the compound (II) is obtainable in a high yield from the compound (I). So, the purification of the reaction product after finishing the reaction is easily effected. For instance, the purification is carried out by washing the reaction mixture with water admixed with a hydrophobic solvent such as chloroform and the like and recrystallizing the crude product obtained by distilling off the solvent, thereby giving the pure compound (II). Namely, the process of the present invention is an extremely profitable industrial process.

The compound (I) used as the starting material in the process of the present invention is synthesized from 4'-demethyl-epipodophyllotoxin (III) (refer to U.S. Pat. No. 3,524,844) which is obtained from an anti-tumour active substance, podophyllotoxin, produced by a plant, *Podophyllum emodi* Wall, for instance, through the following reaction route:

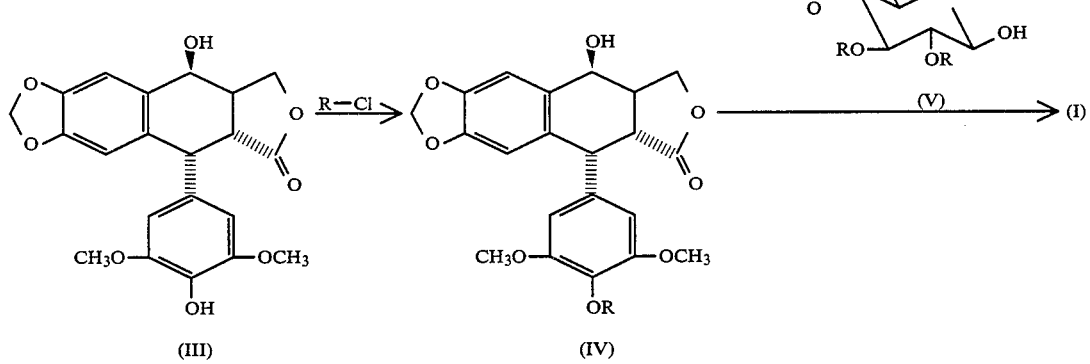

(B) PROCESS FOR REMOVING THE HALOGENOACETYL GROUPS BY SUBJECTING THE COMPOUND (I) TO ALCOHOLYSIS IN THE PRESENCE OF A CATALYST

As the catalyst used in the present invention, zinc chloride, zinc acetate, zinc nitrate, zinc powder, lead acetate, lead powder, cadmium acetate, cobalt acetate, magnesium acetate, calcium acetate, strontium acetate, barium acetate, cerium acetate and the like are preferable and one of them or a combination of more than one of them is used as the catalyst.

wherein R is the same as defined above.

Namely, the compound (I) is obtained by bringing 4'-halogenoacetyl-4'-demethyl-epipodophyllotoxin (IV), which is obtained by reacting a halogenoacetyl chloride with 4'-demethyl-epipodophyllotoxin (III) in an inert solvent, into condensation with 4,6-O-ethylidene-2,3-di-O-halogenoacetyl-β-D-glucopyranose (V) at a temperature of lower than 0° C. in an inert solvent and in the presence of boron trifluoride-ethyl etherate. The compound (V) is a novel compound and is synthesized from 4,6-O-ethylidene-1-O-benzyloxycarbonyl-β-D-glucopyranose (VI) as the starting material, for instance, through the following reaction route:

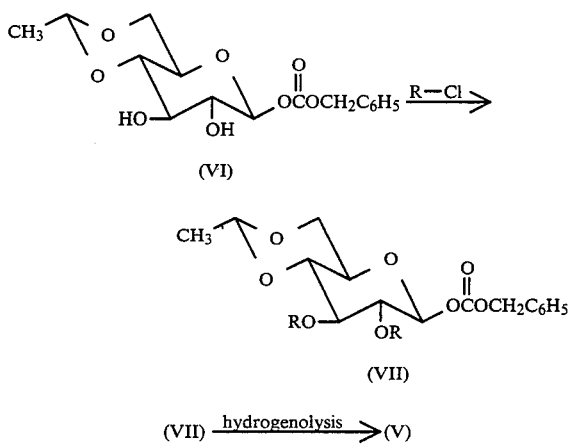

(VII) —hydrogenolysis→ (V)

wherein R is the same as defined above.

Namely, the compound (V) is obtained by subjecting 4,6-O-ethylidene-1-O-benzyloxycarbonyl-2,3-di-O-halogenoacetyl-β-D-glucopyranose (VII) to hydrogenolysis. The compound (VII) is obtained by reacting 4,6-O-ethylidene-1-O-benzyloxycarbonyl-β-D-glucopyranose (VI) with a halogenoacetyl chloride in an inert solvent.

The present invention will be explained more in detail while referring to the following non-limitative Examples.

EXAMPLE 1

1-1: Synthesis of 4'-demethyl-epipodophyllotoxin-β-D-ethylidene-glucoside (II)

8.2 g of 4'-chloroacetyl-4'-demethyl-epipodophyllotoxin-β-D-2,3-di-O-chloroacetyl-4,6-O-ethylidene-glucoside (I) (R=—COCH$_2$Cl) was dissolved in 50 ml of pyridine and the resultant solution was cooled to 0° C. 4.5 g of ethylamine (purity of 70%) was added dropwise thereto and the mixture was stirred for one hour at 0° C. After the reaction was over, 200 ml of chloroform was added to the reaction mixture, and the reaction mixture was neutralized with 2N hydrochloric acid, washed with water and dried on anhydrous sodium sulfate. The crude crystals which were obtained by evaporating the solvent under a reduced pressure from the dried reaction mixture, were recrystallized from chloroform to obtain 4.9 g of crystals in a yield of 83.1%.

The Rf value on TLC (silica gel, a developing solvent mixture of chloroform and methanol of a volume ratio of 9:1), the IR spectrum, the NMR spectrum and the optical rotatory power of the thus obtained crystalline compound were the same as those of the substance obtained according to the process disclosed in Canadian Pat. No. 956,939. Rf was 0.44 and the melting point was 259° to 262° C.

1-2: Synthesis of 4'-demethyl-epipodophyllotoxin-β-D-ethylidene-glucoside (II)

A reaction was carried out in the same manner as in Example 1-1 except for using 4.5 g of pyrrolidine instead of ethylamine. 4.6 g of the compound (II) was obtained in a yield of 78.0%.

1-3: Synthesis of 4'-demethyl-epipodophyllotoxin-β-D-ethylidene-glucoside (II)

A reaction was carried out in the same manner as in Example 1-1 except for using 2.0 g of ethylenediamine of purity of 98% instead of ethylamine in Example 1-1. 4.9 g of the compound (II) was obtained in a yield of 83.1%.

1-4: Synthesis of 4'-demethyl-epipodophyllotoxin-β-D-ethylidene-glucoside (II)

In a solvent mixture of 150 ml of chloroform and 50 ml of methanol, 8.2 g of the compound (I) (R=—COCH$_2$Cl) was dissolved and after adding 6.6 g of diethylamine to the resultant solution, the mixture was stirred for 4 hours at room temperature. By treating the thus stirred reaction mixture in the same manner as in Example 1-1, 3.6 g of compound (II) was obtained in a yield of 61.0%.

1-5: Synthesis of 4'-demethyl-epipodophyllotoxin-β-D-ethylidene-glucoside (II)

In 150 ml of methanol, 8.2 g of the compound (I) (R=—COCH$_2$Cl) was suspended and after adding 10 ml of pyridine and 5.0 g of ammonium acetate to the suspension, the mixture was heated under reflux for one hour. After evaporating methanol from the reaction mixture under a reduced pressure, the residue was treated in the same manner as in Example 1-1 and then 4.5 g of the compound (II) was obtained in a yield of 76.3%.

1-6: Synthesis of 4'-demethyl-epipodophyllotoxin-β-D-ethylidene-glucoside (II)

In a solvent mixture of 150 ml of chloroform and 50 ml of methanol, 8.2 g of the compound (I) (R=—COCH$_2$Cl) was dissolved and after adding 10 ml of triethylamine and 3.5 g of ammonium chloride to the solution, the mixture was stirred for 4 hours at room temperature. After the reaction was over, the reaction mixture was treated in the same manner as in Example 1-1 and then 4.9 g of the compound (II) was obtained in a yield of 83.1%.

1-7: Synthesis of 4'-demethyl-epipodophyllotoxin-β-D-ethylidene-glucoside (II)

A reaction was carried out in the same manner as in Example 1-6 except for using 9.5 g of 4'-bromoacetyl-4'-demethyl-epipodophyllotoxin-β-D-2,3-di-O-bromoacetyl-4,6-O-ethylidene-glucoside (I) (R=—COCH$_2$Br) instead of the compound (I) (R=—COCH$_2$Cl) and then 4.8 g of the compound (II) was obtained in a yield of 81.8%.

EXAMPLE 2

2-1: Synthesis of 4'-demethyl-epipodophyllotoxin-β-D-ethylidene-glucoside (II)

A solution of 8.2 g of 4'-chloroacetyl-4'-demethyl-epipodophyllotoxin-β-D-2,3-di-O-chloroacetyl-4,6-O-ethylidene-glucoside (I) (R=—COCH$_2$Cl) and 1.6 g of anhydrous zinc chloride in 300 ml of methanol was heated under reflux for one hour. After the reaction was over, methanol was distilled off from the reaction mixture, and 200 ml of chloroform was added to the residue and the mixture was washed with water and dried on anhydrous sodium sulfate. By distilling off the solvent under a reduced pressure, crude crystals were obtained and then 4.9 of crystals were obtained by recrystallizing the crude crystals from methanol in a yield of 83.1%.

The Rf value on TLC (silica gel, a developing solvent mixture of chloroform and methanol of a volume ratio of 9:1), the IR spectrum, the NMR spectrum and the optical rotatory power of the thus obtained crystalline compound were the same as those of the substance obtained by the process disclosed in Canadian Patent No. 956,939. Rf was 0.44 and the melting point was 259° to 262° C.

2-2 to 2-14: Synthesis of 4'-demethyl-epipodophyllotoxin-β-D-ethylidene-glucoside (II)

After subjecting 8.2 g of the compound (I) (R=—COCH$_2$Cl) to each reaction condition shown in the following table, the reaction mixture was treated in the same manner as in Example 2-1 and then the compound (II) was obtained in a yield also shown in the following table:

| Example No. | Catalyst name | amount (g) | Amount of methanol (ml) | Time for reflux (hour) | Yield of compound (II) (%) |
|---|---|---|---|---|---|
| 2-2 | Zn(OAc)$_2$ | 4 | 300 | 3 | 81.9 |
| 2-3 | Zn(NO$_3$)$_2$ | 0.8 | 300 | 2 | 81.0 |
| 2-4 | Zn powder | 4 | 300 | 5 | 78.3 |
| 2-5 | Pb(OAc)$_2$ | 1.6 | 300 | 1 | 81.4 |
| 2-6 | Pb powder | 1.6 | 300 | 2 | 76.5 |
| 2-7 | Cd(OAc)$_2$.2H$_2$O | 1.6 | 300 | 3 | 79.1 |
| 2-8 | Co(OAc)$_2$.4H$_2$O | 4 | 800 | 4 | 69.6 |
| 2-9 | Mg(OAc)$_2$ | 12 | 800 | 4 | 72.2 |
| 2-10 | Ca(OAc)$_2$.H$_2$O | 9.6 | 800 | 4 | 67.3 |
| 2-11 | Sr(OAc)$_2$.½H$_2$O | 8 | 800 | 2 | 69.7 |
| 2-12 | Ba(OAc)$_2$ | 8 | 500 | 2 | 70.6 |
| 2-13 | Ce(OAc)$_2$.H$_2$O | 8 | 800 | 2 | 66.4 |
| 2-14 | ZnCl$_2$ Pb(OAc)$_2$ | 0.8 0.8 | 300 | 1 | 82.0 |

2-15: Synthesis of 4'-demethyl-epipodophyllotoxin-β-D-ethylidene-glucoside (II)

A reaction was carried out in the same manner as in Example 2-1 except for using 9.5 g of 4'-bromoacetyl-4'-demethyl-epipodophyllotoxin-β-D-2,3-di-O-bromoacetyl-4,6-O-ethylidene-glucoside (I) (R=—COCH$_2$Br) instead of the compound (I) (R=—COCH$_2$Cl) in Example 2-1 and then 4.8 g of the compound (II) was obtained in a yield of 81.8%.

EXAMPLE A

Synthesis of 4'-chloroacetyl-4'-demethyl-epipodophyllotoxin-β-D-2,3-di-O-chloroacetyl-4,6-O-ethylidene-glucoside (I) (R=—COCH$_2$Cl)

(a) Synthesis of 4'-chloroacetyl-4'-demethyl-epipodophyllotoxin (IV) (R=—COCH$_2$Cl)

After adding 11.9 g of anhydrous pyridine to a suspension of 40.0 g of 4'-demethyl-epipodophyllotoxin (III) in 750 ml of anhydrous ethylene dichloride, the mixture was cooled to −20° C. and then 15.4 g of 95% chloroacetyl chloride was added dropwise to the cooled mixture in 1.5 hours and thereafter the mixture was further stirred for 0.5 hour. After the reaction was over, the reaction mixture was washed with water, and the organic layer was dried on anhydrous sodium sulfate. The crude product which was obtained by distilling off the solvent from the dried organic layer solution under a reduced pressure, was recrystallized from methanol and then 43.4 g of the compound (IV) (R=—COCH$_2$Cl) was obtained in a yield of 91.1%.

The melting point of the thus obtained compound (IV) was 238° to 240° C. and IR absorption bands in a KBr-tablet are set forth below.

IR: $\nu_{max}^{KBr}$ 3550, 1783, 1765(sh), 1483, 1230 and 1130 cm$^{-1}$.

(b) Synthesis of 4,6-O-ethylidene-1-O-benzyloxycarbonyl-2,3-di-O-chloroacetyl-β-D-glucopyranose (VII) (R=—COCH$_2$Cl)

Into a suspension of 51.0 g of 4,6-O-ethylidene-1-O-benzyloxycarbonyl-β-D-glucopyranose (VI) in 500 ml of anhydrous chloroform, 35.6 g of anhydrous pyridine was added and the resultant mixture was cooled to 0° C. After adding 42.8 g of 95% chloroacetyl chloride dropwise to the cooled mixture, the resultant mixture was stirred for 0.5 hour at room temperature. After the reaction was over, the reaction mixture was washed with water and the organic layer was dried on anhydrous sodium sulfate. The crude product which was obtained by distilling off the solvent from the dried organic layer solution under a reduced pressure, was recrystallized from isopropyl ether and then 66.6 g of the compound (VII) (R=—COCH$_2$Cl) was obtained in a yield of 90.1%. The melting point of the thus obtained compound (VII) was 130° to 131° C., IR absorption bands in a KBr-tablet are set forth below.

IR: $\nu_{max}^{KBr}$ 1765, 1255, 1098, 700 cm$^{-1}$.

(c) Synthesis of 4,6-O-ethylidene-2,3-di-O-chloroacetyl-β-D-glucopyranose (V) (R=—COCH$_2$Cl)

In 500 ml of dry acetone, 49.3 g of the compound (VII) (R=—COCH$_2$Cl) was dissolved and 10 g of 10% palladium-charcoal was added to the solution. The mixture was then subjected to hydrogenation under a normal pressure at −15° to −10° C. After the reaction was over, the catalyst was removed by filtration and washed with dry acetone and then, the combined filtrate and washings were condensed at 30° C. under a reduced pressure. The residue was dried at 30° C. under a highly reduced pressure and then 35.6 g of the compound (V) (R=—COCH$_2$Cl) as a white foamy substance was obtained in a yield of 99.2%, IR absorption bands in chloroform are set forth below.

IR: $\nu_{max}^{CHCl_3}$ 3600, 1765, 1282, 1130 and 1095 cm$^{-1}$.

(d) Synthesis of 4'-chloroacetyl-4'-demethyl-epipodophyllotoxin-β-D-2,3-di-O-chloroacetyl-4,6-O-ethylidene-glucoside (I) (R=—COCH$_2$Cl)

In 150 ml of anhydrous ethylene dichloride, 11.9 g of the compound (IV) (R=—COCH$_2$Cl), was dissolved and after adding 9.9 g of the compound (V) (R=—COCH$_2$Cl) into the solution, the mixture was cooled to −20° C. and then 5.3 g of boron trifluoride-ethyl etherate was added dropwise to the thus cooled solution and thereafter the mixture was stirred for 0.5 hour at −20° C. After the reaction was over, 4.0 g of pyridine was added dropwise to the reaction mixture. After washing the resultant mixture with water, the organic layer was dried on anhydrous sodium sulfate. The crude product obtained by distilling off the solvent from the dried organic layer solution was recrystallized from methanol and then 16.4 g of the compound (I) (R=—COCH$_2$Cl) was obtained in a yield of 80.3%.

The melting point of the thus obtained compound (I) (R=—COCH$_2$Cl) was 244° to 246° C. IR absorption bands in a KBr-tablet are set forth below.

IR: $\nu_{max}^{KBr}$ 1775, 1601, 1483, 1232 and 1126 cm$^{-1}$.

EXAMPLE B
Synthesis of 4′-bromoacetyl-4′-demethyl-epipodophyllotoxin-β-D-2,3-di-O-bromoacetyl-4,6-O-ethylidene-glucoside (I) (R=—COCH$_2$Br)

(a) Synthesis of 4′-bromoacetyl-4′-demethyl-epidophyllotoxin (IV) (R=—COCH$_2$Br)

The crude product obtained by the same reaction as in Example A-(a) except for using 20.9 g of 98% bromoacetyl chloride instead of chloroacetyl chloride in Example A-(a) was recrystallized from benzene and 47.0 g of the compound (IV) (R=—COCH$_2$Br) was obtained in a yield of 90.2%. The obtained compound had a melting point of 220° to 222° C. and showed the following IR absorption bands in a KBr-tablet.

IR: $\nu_{max}^{KBr}$ 3540, 1782, 1765, 1601, 1483, 1232 and 1124 cm$^{-1}$.

(b) Synthesis of 4,6-O-ethylidene-1-O-benzyloxycarbonyl-2,3-di-O-bromoacetyl-β-D-glucopyranose (VII) (R=—COCH$_2$Br)

A reaction was carried out in the same manner as in Example A-(b) except for using 53.0 g of 98% bromoacetyl chloride instead of chloroacetyl chloride in Example A-(b) and then 76.2 g of the compound (VII) (R=—COCH$_2$Br) was obtained in a yield of 87.3%. The obtained compound (VII) had a melting point of 140° to 142° C. IR absorption bands in a KBr-tablet are set forth below.

IR: $\nu_{max}^{KBr}$ 1770, 1760, 1243 and 1122 cm$^{-1}$.

(c) Synthesis of 4,6-O-ethylidene-2,3-di-O-bromoacetyl-β-D-glucopyranose (V) (R=—COCH$_2$Br)

A reaction was carried out in the same manner as in Example A-(c) except for using 58.2 g of the compound (VII) (R=—COCH$_2$Br) instead of the compound (VII) (R=—COCH$_2$Cl) in Example A-(c) and 44.4 g of the compound (V) (R=—COCH$_2$Br) as a white foamy substance was obtained in a yield of 98.9%. The thus obtained compound showed the following IR absorption bands in chloroform.

IR: $\nu_{max}^{CHCl_3}$ 3575, 1758, 1275, 1125 and 1095 cm$^{-1}$.

(d) Synthesis of 4′-bromoacetyl-4′-demethyl-epipodophyllotoxin-β-D-2,3-di-O-bromoacetyl-4,6-O-ethylidene-glucoside (I) (R=—COCH$_2$Br)

A reaction was carried out in the same manner as in Example A-(d) except for using 13.0 g of the compound (IV) (R=—COCH$_2$Br) instead of the compound (IV) (R=—COCH$_2$Cl) and using 12.4 g of the compound (V) (R=—COCH$_2$Br) instead of the compound (V) (R=—COCH$_2$Cl) in Example A-(d) and then 18.8 g of the compound (I) (R=—COCH$_2$Br) was obtained in a yield of 79.1%. The thus obtained compound melted at 201° to 203° C. and showed the following IR absorption bands in a KBr-tablet.

IR: $\nu_{max}^{KBr}$ 1770, 1763(sh), 1603, 1483, 1232 and 1120 cm$^{-1}$.

What is claimed is:

1. A process for producing 4′-demethyl-epipodophyllotoxin-β-D-ethylidene-glucoside represented by the formula (II):

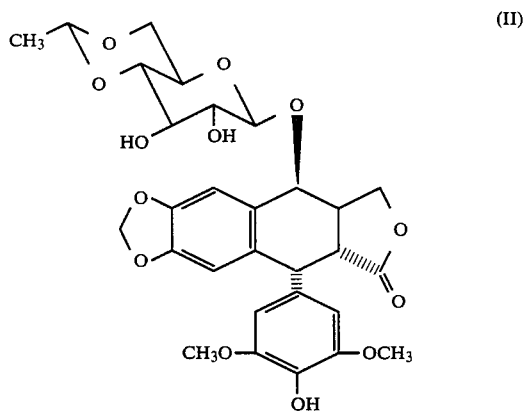

comprising reacting 4′-halogenoacetyl-4′-demethyl-epipodophyllotoxin-β-D-2,3-di-O-halogenoacetyl-4,6-O-ethylideneglucoside represented by the formula (I):

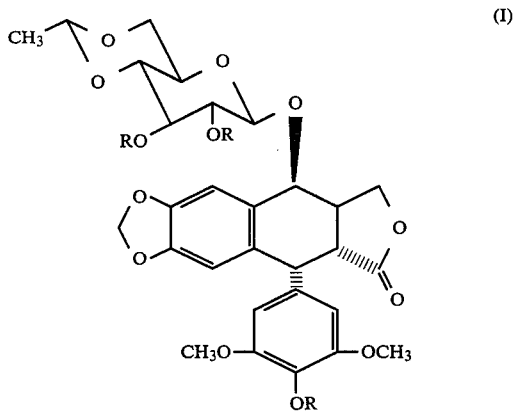

wherein R represents a halogenoacetyl group of the formula

—COCH$_2$X wherein X is a halogen atom, with a material selected from the group consisting of (a) an amine, (b) ammonia, and (c) an amine and ammonia to remove said halogenoacetyl groups of (I), thereby obtaining said 4′-demethyl-epipodophyllotoxin-β-D-ethylidene-glucoside.

2. A process according to claim 1, wherein X is chlorine or bromine.

3. A process according to claim 2, wherein the amine is methylamine, ethylamine, n-propylamine, n-butylamine, dimethylamine, diethylamine, di-n-propylamine, di-n-butylamine, pyrrolidine, piperidine, morpholine or ethylene-diamine.

4. A process according to claim 2 or 3, wherein the reaction is carried out at a temperature of −10° to 100° C.

5. A process for producing 4'-demethyl-epipodophyllotoxin-β-D-ethylidene-glucoside represented by the formula (II):

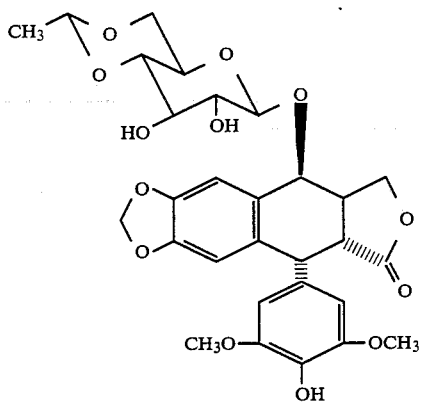

comprising subjecting 4'-halogenoacetyl-4'-demethyl-epipodophyllotoxin-β-D-2,3-di-O-halogenoacetyl-4,6-O-ethylidene-glucoside represented by the formula (I):

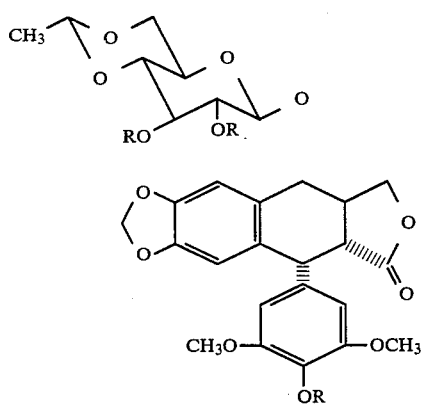

wherein R represents a halogenoacetyl group of the formula

—COCH$_2$X wherein X is a halogen atom, to alcoholysis in methanol, ethanol or propanol in the presence of the catalyst which is one or more than one member selected from the group consisting of zinc chloride, zinc acetate, zinc nitrate, zinc powder, lead acetate, lead powder, cadmium acetate, cobalt acetate, magnesium acetate, calcium acetate, strontium acetate, barium acetate and cerium acetate, to remove said halogenoacetyl groups, thereby obtaining said 4'-demethyl-epipodophyllotoxin-β-D-ethylidene-glucoside.

6. A process according to claim 5, wherein X is chlorine or bromine.

7. A process according to claim 5 or 6 wherein the alcoholysis is carried out at a temperature of 40° to 100° C.

8. 4'-Halogenoacetyl-4'-demethyl-epipodophyllotoxin-β-D-2,3-di-O-halogenoacetyl-4,6-O-ethylidene-glucoside represented by the formula:

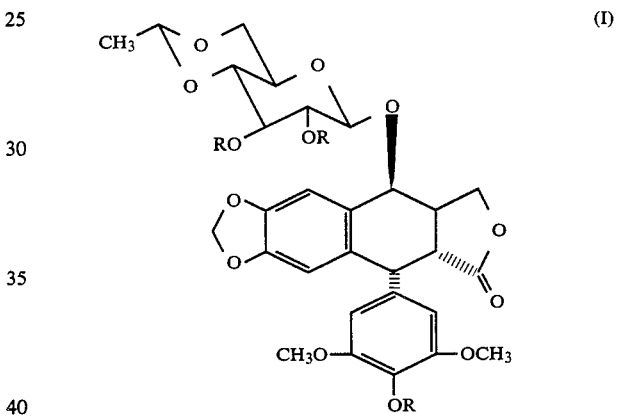

wherein R represents a halogenoacetyl group of the formula

—COCH$_2$X wherein X is a halogen atom.

9. A compound according to claim 8, wherein X is chlorine or bromine.

* * * * *